United States Patent
Hwang

(10) Patent No.: US 6,193,662 B1
(45) Date of Patent: Feb. 27, 2001

(54) HIGH FRAME RATE PULSE INVERSION HARMONIC ULTRASONIC DIAGNOSTIC IMAGING SYSTEM

(75) Inventor: Juin-Jet Hwang, Mercer Island, WA (US)

(73) Assignee: ATL Ultrasound, Bothell, WA (US)

( * ) Notice: Subject to any disclaimer, the term of this patent is extended or adjusted under 35 U.S.C. 154(b) by 0 days.

(21) Appl. No.: 09/251,563

(22) Filed: Feb. 17, 1999

(51) Int. Cl.7 .................................................. A61B 8/00
(52) U.S. Cl. ................................. 600/447; 600/458
(58) Field of Search ................................... 600/437, 443, 600/447, 458; 73/625–626; 367/7, 11, 103–105

(56) References Cited

U.S. PATENT DOCUMENTS

| | | |
|---|---|---|
| 4,549,210 | 10/1985 | Dulapa . |
| 5,318,033 | 6/1994 | Savord . |
| 5,390,674 | 2/1995 | Robinson et al. . |
| 5,431,167 | 7/1995 | Savord . |
| 5,462,057 | 10/1995 | Hunt et al. . |
| 5,577,505 | 11/1996 | Brock-Fisher et al. . |
| 5,623,928 | 4/1997 | Wright et al. . |
| 5,632,277 | 5/1997 | Chapman et al. . |
| 5,667,373 | 9/1997 | Wright . |
| 5,706,819 | 1/1998 | Hwang et al. . |
| 5,902,243 | 5/1999 | Holley et al. . |
| 5,980,458 | * 11/1999 | Clark .................................. 600/437 |
| 6,099,471 | * 8/2000 | Torp et al. ........................ 600/438 |
| 6,117,082 | * 9/2000 | Bradley et al. ................... 600/447 |

FOREIGN PATENT DOCUMENTS

99/30617   6/1999  (WO) .

* cited by examiner

Primary Examiner—Francis J. Jaworski
(74) Attorney, Agent, or Firm—W. Brinton Yorks, Jr.

(57) ABSTRACT

An ultrasonic diagnostic imaging system and method are provided for producing harmonic ultrasonic images at high line densities or frame rates of display. Scanlines are received from spatially adjacent fundamental frequency transmit beams of opposite phase or polarity. The received scanlines are summed on a spatially consistent basis to produce image lines of separated harmonic echo signals intermediate the adjacent scanlines. The received scanlines may be subtracted, or the polarity of alternately received scanlines inverted, to produce image lines of separated linear (fundamental frequency) echo signals. In preferred embodiments the received scanlines are combined by filter functions which reduce or eliminate artifacts which otherwise arise from the scanline combining process.

27 Claims, 15 Drawing Sheets

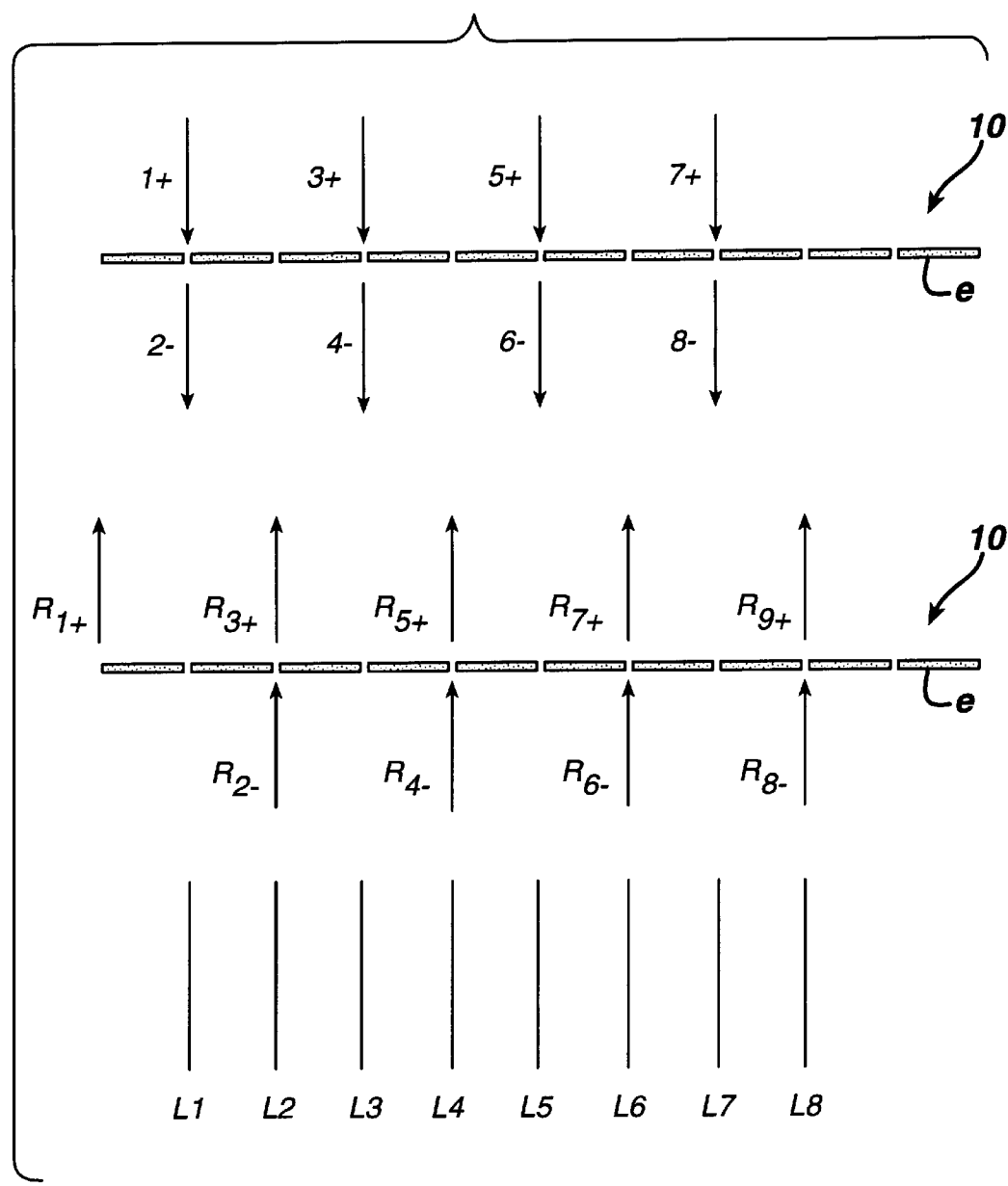

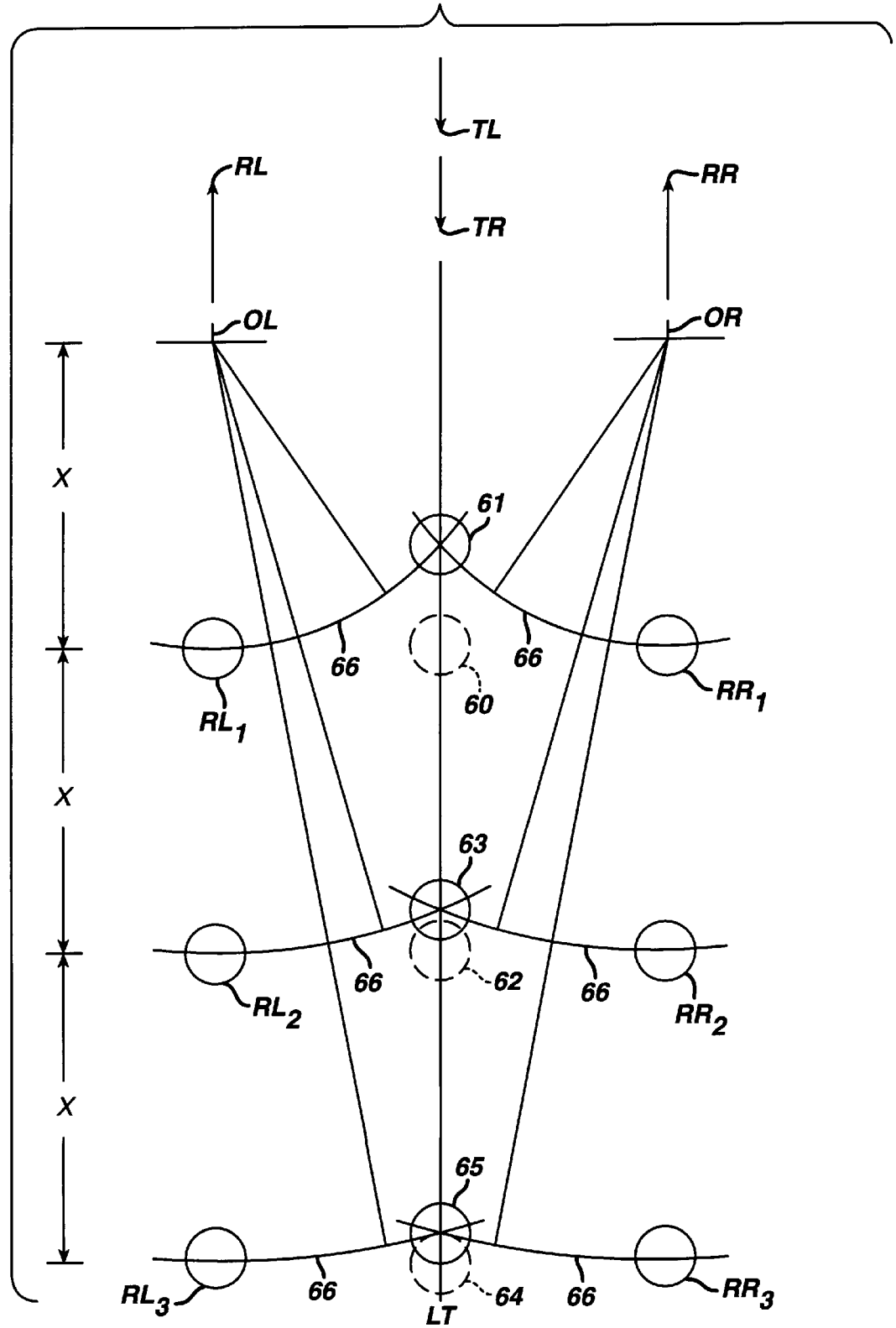

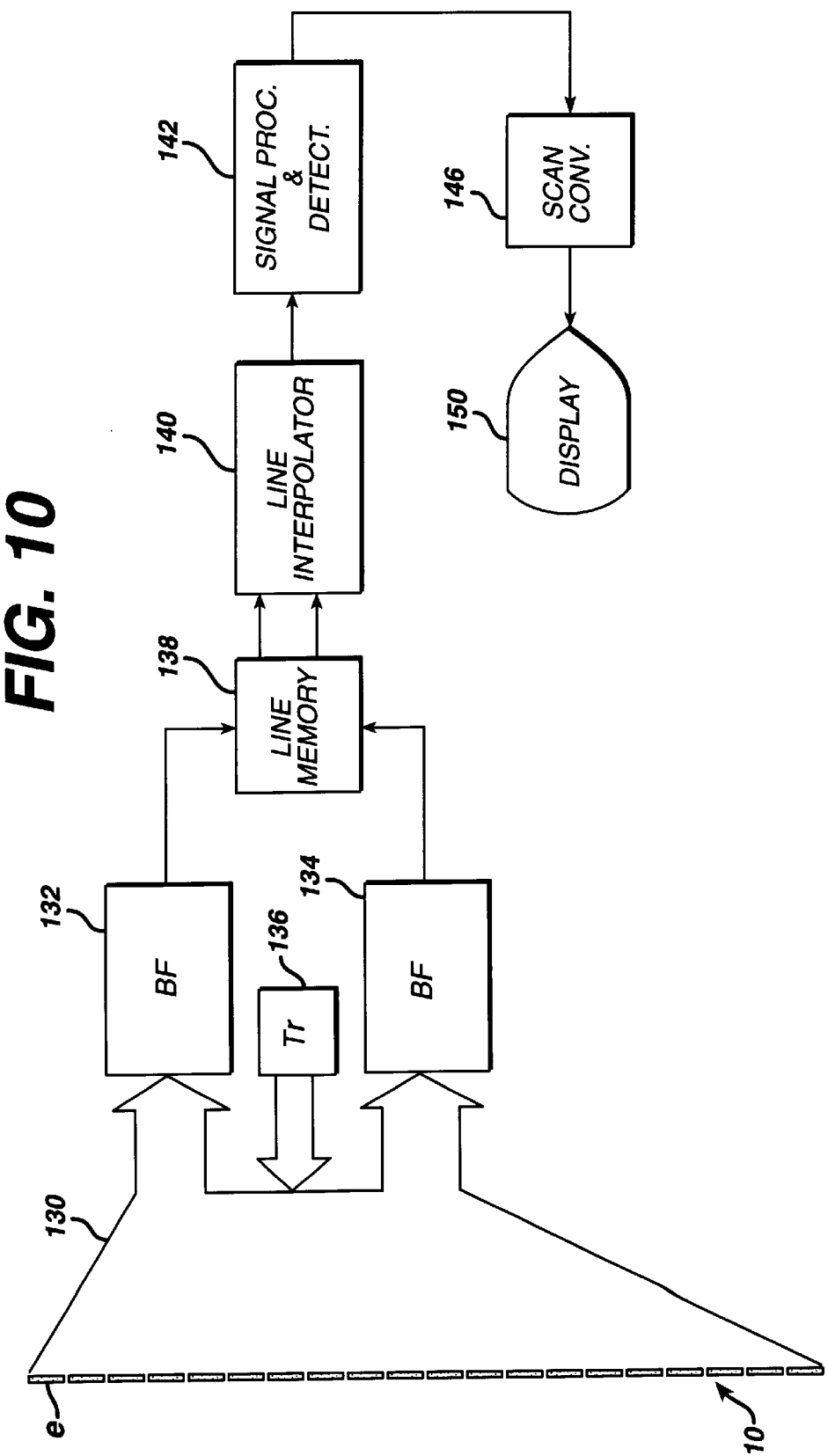

HIGH FRAME RATE PULSE INVERSION HARMONIC ULTRASONIC DIAGNOSTIC IMAGING SYSTEM

This invention relates to ultrasonic diagnostic imaging systems and, in particular, to pulse inversion harmonic ultrasonic diagnostic imaging at high frame rates or line densities of display.

U.S. Pat. No. 5,706,819, of which I am a co-inventor, describes a signal processing technique which separates fundamental and harmonic signal components in received ultrasonic echo signals. This technique, known in ultrasound as "pulse inversion," is a two pulse technique in which two pulses of opposing polarity (phase) are successively transmitted to the same location in the body. Echoes are received following each transmission in which fundamental signal components are out of phase due to the opposing polarity of the transmit pulses, but the higher order harmonic signal components, being quadratic in nature, are not. Summing the two echoes will cancel the opposing fundamental components and reinforce the harmonic components, leaving a cleanly separated harmonic signal without the need for conventional filters. Subtracting the two echoes will have the opposite result, canceling the harmonic signal components and reinforcing the fundamental (linear) signal components. In a similar manner, subtraction leaves a cleanly separated fundamental echo signal.

Pulse inversion is a two pulse technique, however, meaning it is necessary to scan each acoustic line twice in order to form a single image. This means that the time required to acquire all of the scanlines of an image is approximately doubled as compared to conventional single pulse imaging. The time to acquire all of the scanlines of an image frame determines the frame rate of display, which will approximately halve with a two pulse technique. It is desirable to have as high a frame rate as possible so that realtime imaging is produced which shows tissue motion smoothly and with little interframe discontinuity as a scanhead is moved when surveying a patient's anatomy.

In accordance with the principles of the present invention, pulse inversion harmonic imaging is carried out at a high frame rate of display and a high line density. In the inventive technique transmit pulses of opposing polarity (phase) are transmitted along transmit scanlines at adjacent positions in the image field. The received scanlines are combined to separate harmonic signals on image lines which are intermediate the positions of the transmitted scanlines. In one embodiment transmit scanlines are paired to overlap, enabling the formation of image lines of separated harmonic signals at and between the positions of the transmitted scanlines. The spacing of the transmitted scanlines can be varied to vary both the line density of the ultrasonic image and the image frame rate of display. In another embodiment transmit pulses of opposing polarity (phase) are transmitted and multiple scanlines are received in response to each transmitted scanline. Received scanlines from opposite polarity pulses are combined to produce harmonic images at a high frame rate of display. By combining received scanlines in a temporally consistent manner, motion artifacts are reduced. In yet another embodiment received scanlines are combined both additively and differentially to simultaneously produce separated fundamental and harmonic scanline signals, which may then be variably blended together to form images which take advantage of the characteristics of both fundamental and harmonic signal information.

In the drawings:

FIG. 3 illustrates a variation of the pulse inversion scanning technique of FIG. 2;

FIGS. 3A–3D illustrate the development and removal of artifacts associated with the scanning technique of FIG. 3;

FIG. 10 illustrates in block diagram form an ultrasonic diagnostic imaging system which produces images with reduced motion artifacts in accordance with the inventive technique of FIG. 9.

Figure 1:
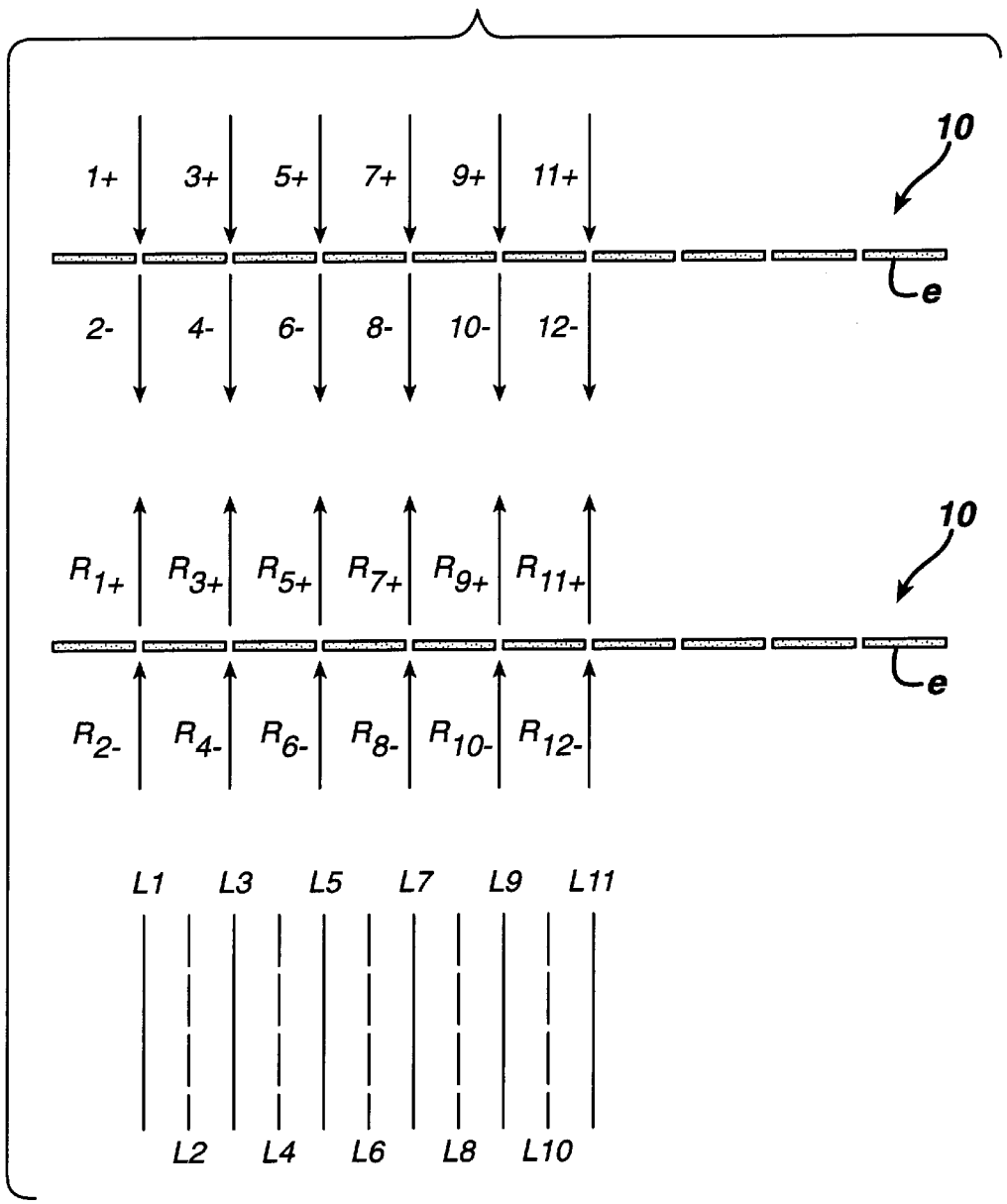
FIG. 1 illustrates a pulse inversion scanning technique of the present invention which produces a high line density image.

Referring first to FIG. 1, a pulse inversion scanning technique of the present invention is shown. In FIGS. 1–4 and 9 the vectors of an image field (the region of the body which is being scanned) along which ultrasonic waves are transmitted and received are represented by arrows. These scanline arrows are shown in a relative spatial orientation in relation to the elements e of a linear array transducer 10 which transmits and receives the scanlines. The scanlines are depicted in a linear format, however they may also be transmitted and received in a sector or steered linear format as is known in the art. Scanline arrows pointing down in these drawings depict transmit scanlines and scanline arrows pointing up depict received scanlines. Straight lines depict image lines in their relative positions in an image.

In pulse inversion scanning in accordance with my aforementioned patent, two pulses of opposing phase or polarity are transmitted along each scanline direction, as represented by the paired transmit scanlines, the first pair of which is shown by transmit scanlines 1+ and 2−, with the "+" indicating a positive polarity transmit pulse and the "−" indicating a negative polarity transmit pulse. The relative phase opposition of the two transmit pulses or waveforms is preferably 180°; a lesser difference yields less than complete separation of linear and harmonic signal components when the resulting echoes are combined.

When pulse inversion is performed as shown in my patent, transmit scanlines 1+ and 2− yield received scanlines $R_{1+}$ and $R_{2-}$, respectively, with the number indicating the corresponding transmit scanline. Transmit scanlines 3+ and 4− yield received scanlines $R_{3+}$ and $R_{4-}$, and so forth along the array. Echoes along each received scanline are then summed or added on a common depth (z) basis to cancel fundamental signal components from tissue or contrast agents and leave only the harmonic signal components of the received echoes. Thus, the summation of received scanlines $R_{1+}$ and $R_{2-}$ produces an image line L1 of harmonic signals, the summation of received scanlines $R_{3+}$ and $R_{4-}$, produces an image line L3 of harmonic signals, and so forth.

In accordance with the principles of the present invention adjacent scanlines received from transmit scanlines of opposite polarity are summed to produce separated harmonic echo signals along image lines which are intermediate the adjacent scanlines. Received scanlines $R_{2-}$ and $R_{3+}$ are summed to produce harmonic echo signals along image line L2 which is intermediate image lines L1 and L3. Received scanlines $R_{4-}$ and $R_{5+}$ are summed to produce harmonic echo signals along image line L4 which is intermediate image lines L3 and L5, and so on across the image field. It is seen that this further combination of adjacent scanlines produces a harmonic image with twice the line density of conventional pulse inversion imaging, using the same transmit pulse sequence as the conventional technique.

It will be appreciated that adjacent received scanlines $R_{1+}$ and $R_{4-}$ could also be used to separate the harmonic echoes of image line L2 since this pair of adjacent scanlines, like the $R_{2-},R_{3+}$ pair, results from oppositely phased transmit pulses. However, since the $R_{1+},R_{4-}$ pair is separated by the transmit-receive intervals of two other scanlines, 2− and 3+ and their received echoes, the $R_{1+},R_{4-}$ pair is more susceptible to motion artifacts than is the time sequential $R_{2-}$, $R_{3+}$ pair. Hence in the preferred embodiment time sequential adjacent scanlines are used to form the even-numbered intermediate image lines.

Figure 5:
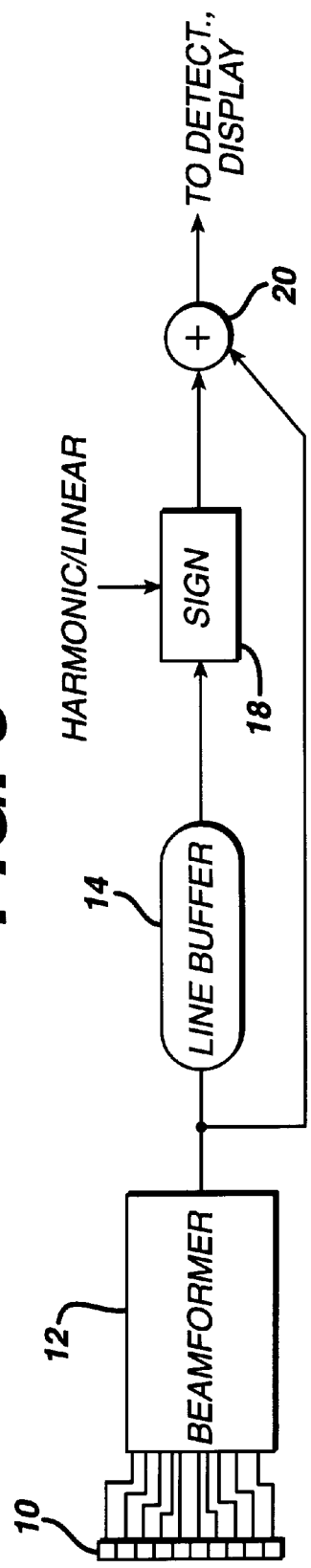
FIG. 5 illustrates in block diagram form the receiver of an ultrasonic diagnostic imaging system for processing signals in accordance with the inventive technique of FIGS. 1–3.

The received scanline processing arrangement of FIG. 5 may be used to form the image lines shown in FIG. 1. Echoes are received by the transducer array 10 following each transmit scanline and coherent echo signals are steered and focused by a receive beamformer 12 to produce a sequence of echo signals along the received scanline. Each received scanline is coupled to a line buffer 14 which delays each scanline by the time interval of a transmit-receive cycle such that the previous receive scanline and the current receive scanline are simultaneously applied to a summer 20. The summer 20 will therefore sum echoes of the two scanlines on a corresponding depth (z) basis, producing separated harmonic echo signals. When the sign of one of the signals being combined is changed by a sign change circuit 18, the arrangement of FIG. 5 will produce separated linear signals, as indicated by the harmonic/linear control signal applied to the sign change circuit. An alternate way to achieve the same result is to replace the summer 20 with a difference circuit (subtractor). The separated harmonic or linear signals are then coupled to subsequent processing circuitry of the ultrasound system where the echo signals are detected, processed, and displayed in the usual manner.

Since the processing system of FIG. 5 processes pairs of sequentially received scanlines, the summer 20 can produce the following combinations, depending upon the setting of the sign change circuit:

Harmonic components:

L1=$(R_{1+}+R_{2-})$; L2=$(R_{2-}+R_{3+})$; L3=$(R_{3+}+R_{4-})$; L4=$(R_{4-}+R_{5+})$; ...

Linear components:

L1=$(R_{1+}-R_{2-})$; L2=$(-R_{2-}+R_{3+})$; L3=$(R_{3+}-R_{4-})$; L4=$(-R_{4-}+R_{5+})$; ...

This operation is equivalent to convolving a spatial filter of the form [1 1] with the received data that is acquired by alternating the polarity (or phase) of the transmit pulse. Harmonic components and linear components are separated by inverting/noninverting the sign of the received data prior to the convolution.

Figure 2:
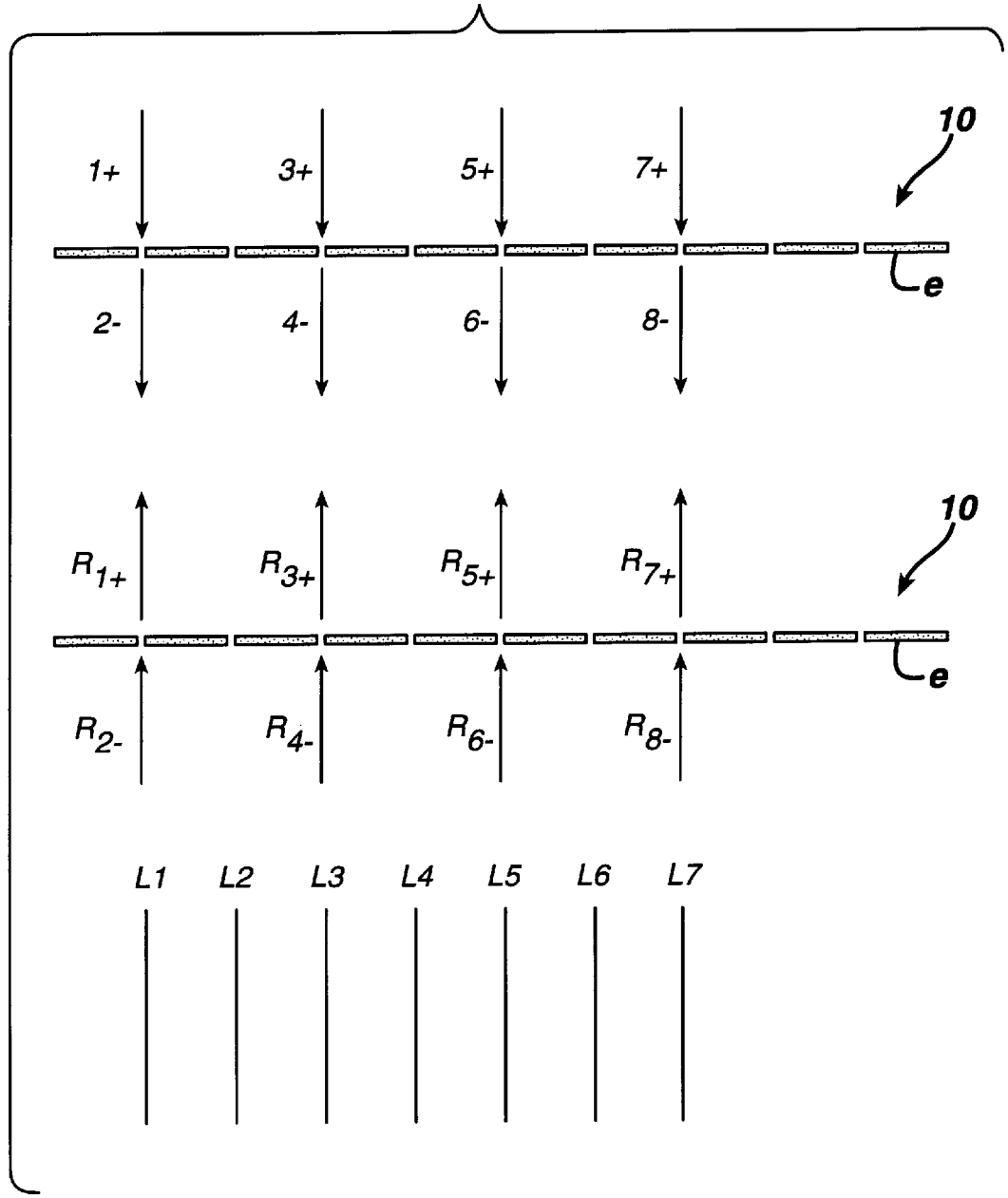
FIGS. 2 and 2A illustrate pulse inversion techniques of the present invention which produce ultrasonic images at a high frame rate of display.

In FIG. 2 the lateral spacing of the transmitted and received scanlines is doubled in comparison with the FIG. 1 embodiment. In the same manner as FIG. 1, transmit scanlines 1+ and 2− yield received scanlines $R_{1+}$ and $R_{2-}$, respectively, transmit scanlines 3+ and 4− yield received scanlines $R_{3+}$ and $R_{4-}$, and so forth along the array 10, but at a two element spacing instead of a single element spacing. The received scanlines are processed by the processing system of FIG. 5 in the same manner as before, producing image lines L1, L2, L3, L4, ... of harmonic echo information but, due to the doubled scanline spacing, the image lines are of the same line density as the conventional pulse inversion technique. Compare the image line spacing of FIG. 2 with the image line spacing of the odd-numbered image lines of FIG. 1. But since scanlines are transmitted and received at twice the spacing as in FIG. 1, only half as many transmit-receive intervals are required and the image lines for a full image frame at the conventional image line density are acquired in half the time. Thus, the frame rate of an image produced in accordance with the scanning sequence of FIG. 2 is twice the conventional pulse inversion frame rate.

Figure 2A:
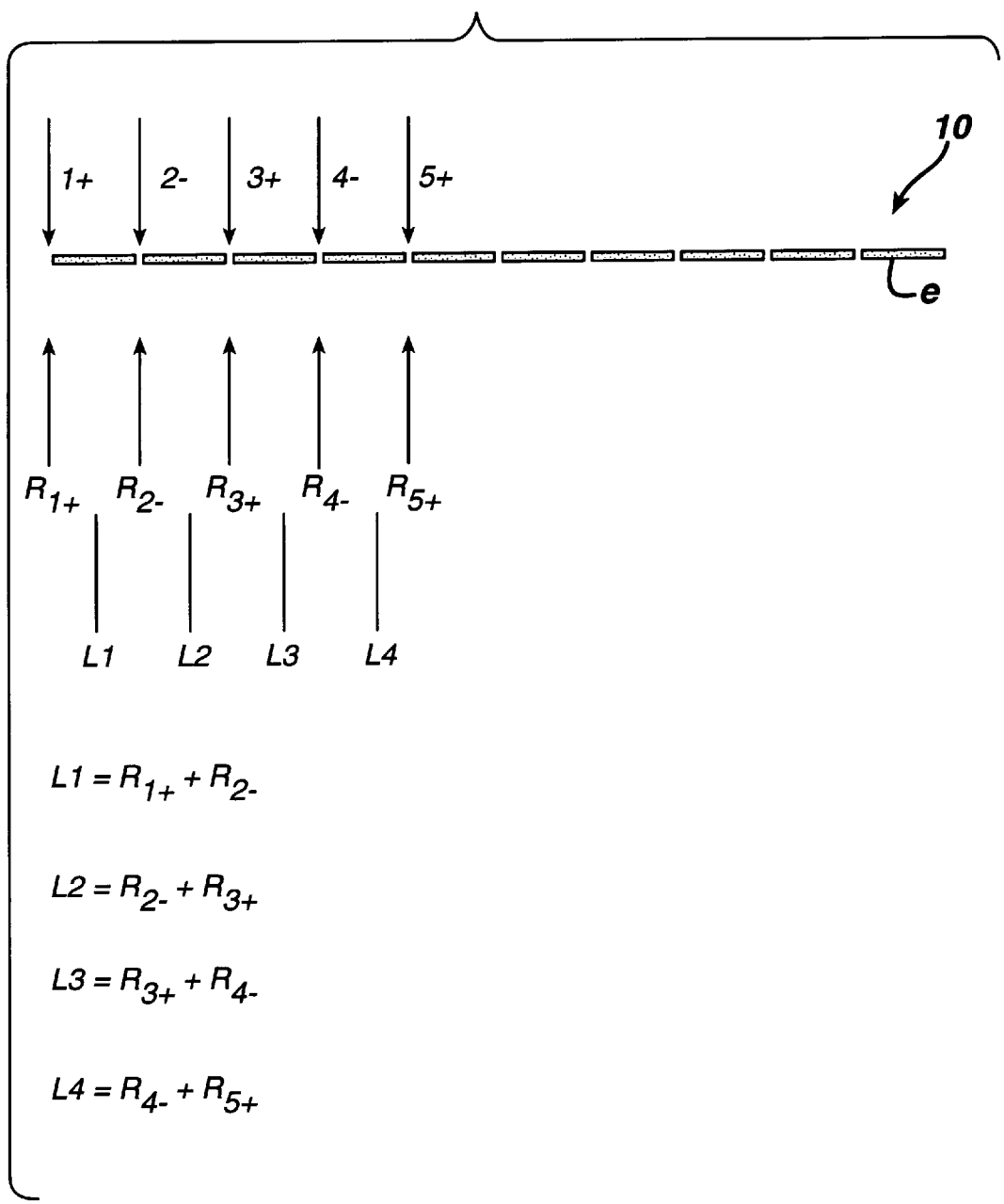

If the paired received scanlines (e.g., $R_{1+},R_{2-}$ in FIG. 2) are offset from each other rather than being co-aligned as shown in FIGS. 1 and 2, the combination of the two received scanlines will produce an image line of harmonic echoes at a line location intermediate that of the received scanlines. Thus, one could combine laterally offset scanlines $R_{1+}$ and $R_{2-}$ to form an intermediate image line of harmonic echoes, then combine laterally offset scanlines $R_{2-}$ and $R_{3+}$ to form an intermediate image line of harmonic echoes, then combine laterally offset scanlines $R_{3+}$ and $R_{4-}$ to form an intermediate image line of harmonic echoes, and so forth, as shown in FIG. 2A.

The present inventor has found that the scanning techniques of FIGS. 1 and 2 can develop an artifact due to the line to line aperture variation. In FIG. 2, for instance, it is seen that each pair of spatially aligned receive scanlines such as $R_{1+}$ and $R_{2-}$ are spatially aligned with each other and with their respective transmit scanlines. That is, both the transmit and receive apertures for the scanlines which are combined are commonly aligned and in spatial alignment with the resultant odd-numbered image line. But the even-numbered image lines are formed by combining scanlines from unaligned apertures. For example, received scanline $R_{2-}$ and its transmit scanline are centered between the first and second elements e of the array 10 while received scanline $R_{3+}$ and its transmit scanline are centered between the third and fourth elements of the array. Thus, each image line across the image field is alternately formed from echoes from aligned and unaligned apertures. This alternation across the image can result in an annoying "picket fence" artifact in the image, particularly in the case of motion in the image field.

One approach to reducing this picket fence artifact is to filter, or average, consecutively received scanlines. Filtered image lines with reduced artifacts may be produced by convolving a filter of the form [1 2 1] with the received scanline data acquired from alternate polarity transmit pulses. As in the case of the arrangement of FIG. 5, either harmonic or linear components may be separated by selectively inverting or noninverting the sign of the received data prior to convolution. The [1 2 1] filter will produce the following image lines:

Harmonic components:

L1=$(R_{1+}+2R_{2-}+R_{3+})$; L2=$(R_{2-}+2R_{3+}+R_{4-})$; L3=$(R_{3+}+2R_{4-}+R_{5+})$; L4=$(R_{4-}+2R_{5+}+R_{6-})$; ...

Linear components:

L1=$(R_{1+}-2R_{2-}+R_{3+})$; L2=$(-R_{2-}+2R_{3+}-R_{4-})$; L3=$(R_{3+}-2R_{4-}+R_{5+})$; L4=$(-R_{4-}+2R_{5+}-R_{6-})$; ...

Consistent with the principle of pulse inversion, it is seen that each of the separated components is composed of an equal contribution of echoes from both positive and negative (opposite polarity) transmit pulses. For instance, harmonic image line L1 is composed of two samples from positive transmit pulses ($R_{1+}$ and $R_{3+}$) and two samples from negative transmit pulses ($2R_{2-}$).

Figure 6:
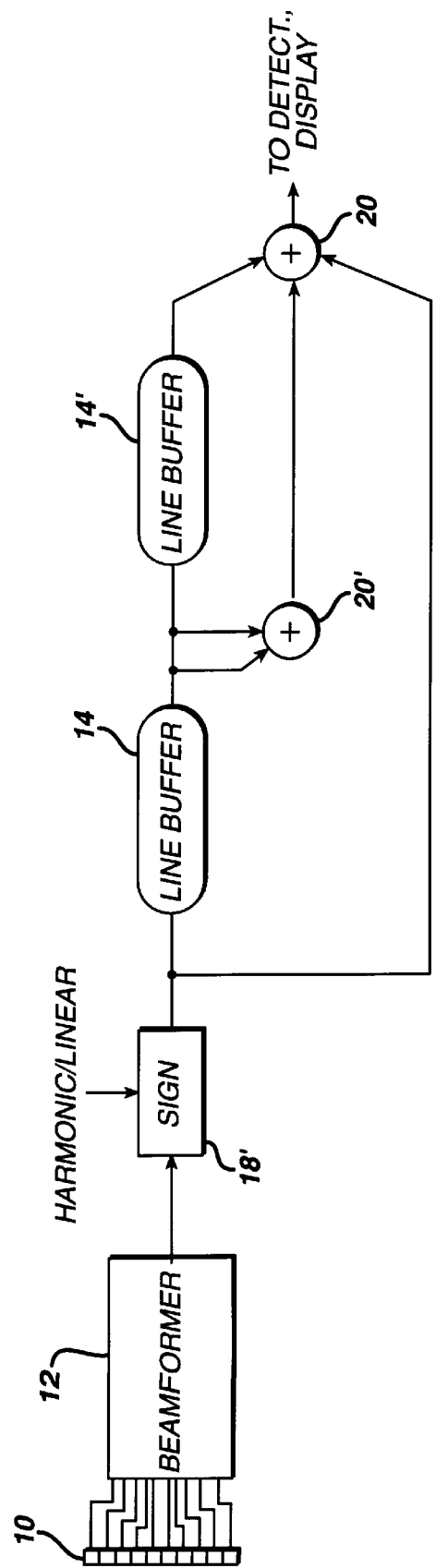
FIG. 6 illustrates in block diagram form the receiver of an ultrasonic diagnostic imaging system which employs a [1 2 1] filter function.

An arrangement which implements the foregoing [1 2 1] filter is shown in FIG. 6. This arrangement is similar to that of FIG. 5, but includes a second line buffer 14' to twice-delay received scanlines and a second summer 20' which produces the $2R_{xx}$ term for the [1 2 1] filter function. In this embodiment the sign change circuit 18' functions by passing received data without alteration when harmonic components are being produced, and by changing the sign of alternate received scanlines when linear components are being produced. From the form of the linear components shown above, it is seen that the signs of the even-numbered received scanlines are inverted ($R_{2-}$, $R_{4-}$, etc.) and the signs of the odd-numbered received scanlines ($R_{1+}$, $R_{3+}$, $R_{5+}$) are unchanged. This operation of the sign changing circuit of changing the sign of alternate lines is also effective for the embodiment of FIG. 5.

Another scanning technique for high frame rate pulse inversion imaging is shown in FIG. 3. In this embodiment each received scanline is received at an aperture offset from the transmit aperture by one element spacing. For instance, the echoes from transmit scanline 1+ are received at a received scanline $R_{1+}$ aperture which is offset one element to the left of its transmit aperture, and the echoes from transmit scanline 2− are received at a received scanline $R_{2-}$ aperture which is offset one element to the right of its transmit aperture. Likewise, the echoes from transmit scanline 3+ are received at a received scanline $R_{3+}$ aperture which is offset one element to the left of its transmit aperture, and the echoes from transmit scanline 4− are received at a received scanline $R_{4-}$ aperture which is offset one element to the right of its transmit aperture, and so on. When image line L1 is formed from received scanlines $R_{1+}$ and $R_{2-}$, it is seen that the image line is in alignment with one aperture, the transmit aperture, but the other aperture, the receive aperture, is split on either side of the position of the image line. In like manner, while image line L2 is in alignment with one aperture, in this case the receive apertures of scanlines $R_{2-}$ and $R_{3+}$, the transmit apertures of scanlines 2− and 3+ are split on either side of the position of the image line. Thus there is a common characteristic across the image field: each image line is in alignment with one aperture (transmit or receive) and unaligned with the other (which is split one element to either side of the image line.) While no image line is in complete alignment with both apertures, the uniformity of the aperture nonalignment across the image field will reduce the artifact resulting from the alternating aperture characteristics of FIGS. 1 and 2.

In digital ultrasound systems, received echoes are dynamically focused and temporally sampled. Such a sampled data system exhibits certain characteristics which require specific processing to avoid image artifacts. In particular, when the scanning technique of FIG. 3 is implemented in a digital ultrasound system, interpolated samples on image lines aligned with the transmit aperture are misaligned row by row with interpolated samples on image lines aligned with the receive aperture.

Figure 3B:
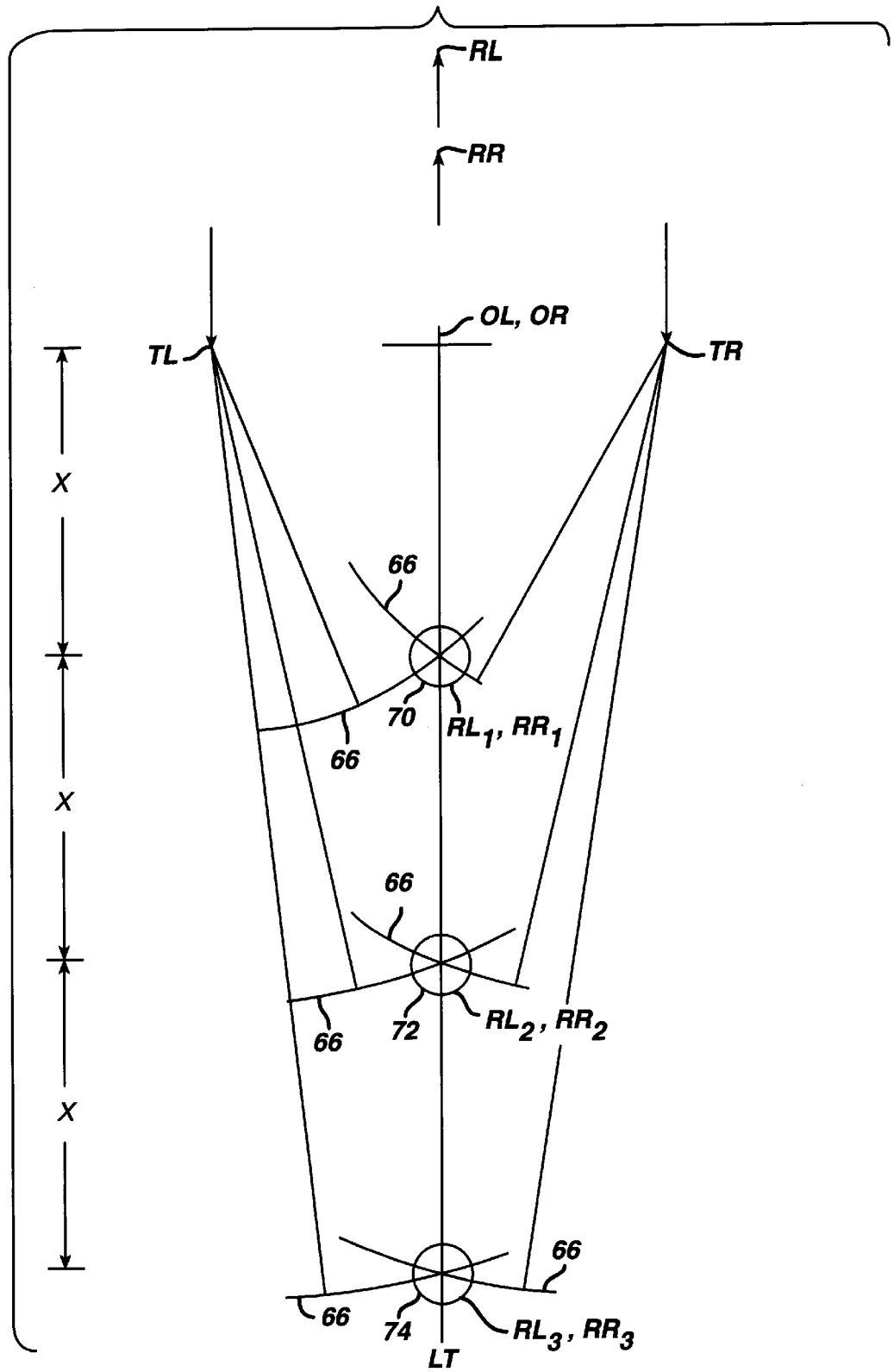
Figure 3C:
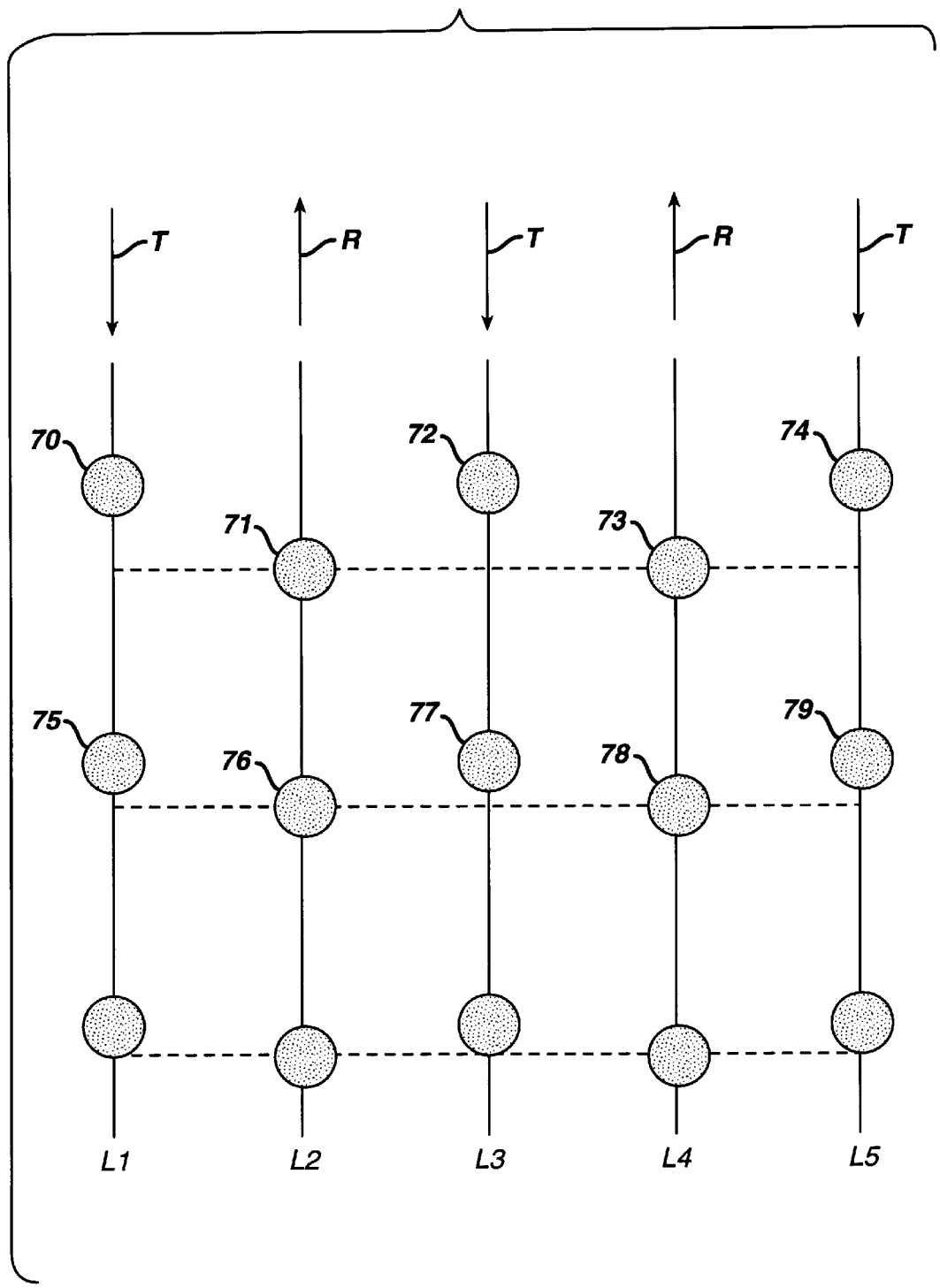

FIGS. 3A–3C illustrate this problem. In FIG. 3A, transmit apertures TL and TR are aligned with an image line LT. The respective receive apertures OL and OR are located to the left and to the right of the transmit apertures. Echo data samples $RL_x$ and $RR_x$ are received from apertures OL and OR at uniformly spaced distances (or uniformly spaced times) x in the image field. When these data samples $RL_x$ and $RR_x$ are combined to interpolate image line samples at the desired intermediate locations 60, 62, 64 in line with the transmit aperture, the resultant interpolated samples are not uniformly spaced but are located on the intersections of the isochrons 66 of the respective receive apertures as shown by interpolated samples 61, 63, and 65.

FIG. 3B illustrates the spacing of the samples when the interpolated image line is aligned with the receive apertures. The transmit apertures TL and TR are located to the left and right of the aligned receive apertures OL and OR. Echo data samples $RL_x$ and $RR_x$, being received from aligned received apertures OL and OR, will result in uniformly spaced image line samples 70, 72, 74. This drawing shows that interpolated samples from aligned receive apertures will remain uniformly spaced.

When the interpolated samples of FIGS. 3A and 3B are combined in an image field, it is seen that the spacing of the image line samples varies from one image line to the next across the image field, as shown by FIG. 3C. Image line samples aligned with the transmit apertures exhibit one spacing, and image line samples aligned with the receive apertures exhibit another spacing. These unregistered image samples will result in a "shimmering" artifact, particularly in the near field of the resultant image where the misregistration is the most severe.

One way to remedy this shimmering artifact problem is to employ a signal resampling process.

Axial resampling can recalculate sample values at the desired locations along the image line using the values of the acquired, misregistered samples of the image line. The resampling process can create its own artifact if only the misregistered image lines are resampled, for this will alter the bandwidth from line to line. Such artifacts can be reduced by employing a double resampling process on all image lines, computing intermediate values first, and then final values at the desired sample locations on the lines, or by resampling all image lines to a sample alignment different from that of both types of received sample alignments. Since the pulse inversion process is a linear operation, the resampling process can be implemented before or after harmonic/linear separation.

The shimmering artifact can also be eliminated by processing the received scanlines using a spatial filter. Previous examples have demonstrated the use of [1 1] and [1 2 1] filters. In the case of the [1 2 1] filter it is seen that $$R_{1+}+2R_{2-}+R_{3+}=(R_{1+}+R_{2-})+(R_{2-}+R_{3+})$$

This shows that the effect of applying a [1 2 1] filter is equivalent to averaging the transmit aligned pixel with the receive aligned pixel to reduce the image artifact. But the [1 2 1] filter will only reduce, not eliminate, the artifact since the transmit and receive pixel apertures are not perfectly aligned.

Figure 3D:
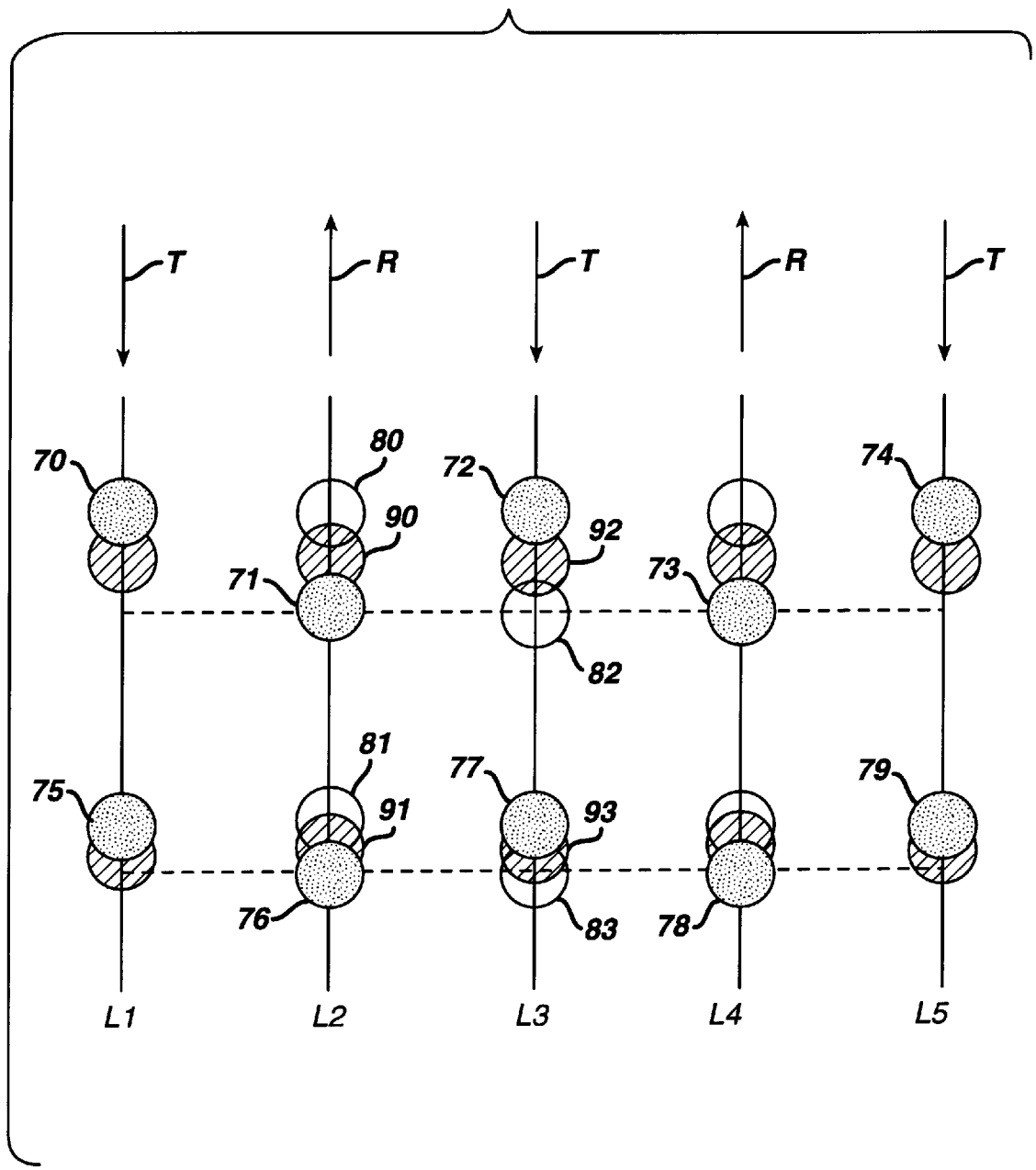

A higher order [1 3 3 1] filter will effectively eliminate the artifact, however, as illustrated by FIG. 3D. In this drawing the samples 70–79 show the alternate alignment of image line pixel data as a result of [1 1] filtering, as in FIG. 3C. The odd-numbered image lines are aligned with the transmit scanlines and the even-numbered image lines are aligned with the received scanlines and the scanlines are equally laterally spaced as a result of the scanning format of FIG. 3. To register this image data laterally, each pair of consecutive transmit-aligned scanlines is interpolated to produce intermediate pixel data aligned with the receive-aligned scanlines, and each pair of consecutive receive-aligned scanlines is interpolated to produce intermediate pixel data aligned with the transmit-aligned scanlines. This intermediate pixel data is then averaged with the axially adjacent sample data to produce the desired image data.

As an example, the data on lines L1, L2 and L3 is initially of the form:

L1: $(R_{1+}+R_{2-})$ L2: $(R_{2-}+R_{3+})$ L3: $(R_{3+}+R_{4-})$

From the two adjacent scanlines aligned with the transmit beams, L1 and L3, intermediate interpolated scanline data 80,81 is produced:

$(L1+L3)/2$: $0.5((R_{1+}+R_{2-})+(R_{3+}+R_{4-}))$

This intermediate interpolated data is axially interpolated with the uninterpolated data on the receive aligned scanline L2 to produce the desired aligned interpolated pixels 90,91:

$(L1+L3)/4+L2/2=L1/4+L3/4+L2/2$: $0.25(R_{1+}+3R_{2-}+3R_{3+}+R_{4-})$

In the same manner, intermediate interpolated scanline data 82,83 is produced from adjacent scanlines aligned with the received scanlines:

$(L2+L4)/2$: $0.5((R_{2-}+R_{3+})+(R_{4-}+R_{5+}))$

This intermediate interpolated data is axially interpolated with the uninterpolated data on the transmit aligned scanline L3 to produce desired aligned interpolated pixels 92,93:

$(L2+L4)/4+L3/2=L2/4+L4/4+L3/2$: $0.25(R_{2-}+3R_{3+}+3R_{4-}+R_{5+})$

Neglecting the scaling factor of 0.25, the aligned pixels are of the form

L2: $R_{1+}+3R_{2-}+3R_{3+}+R_{4-}$ L3: $R_{2-}+3R_{3+}+3R_{4-}+R_5$

This is effectively equivalent to processing the scanline data with a [1 3 3 1] filter. The preceding example describes the processing to separate harmonic image line data. Linear image line data can be obtained by inverting the sign of the received data acquired in response to the transmit pulses of inverted (negative) sign or polarity. The separated linear components will thus be of the form

L2: $R_{1+}-3R_{2-}+3R_{3+}-R_{4-}$ L3: $-R_{2-}+3R_{3+}-3R_{4-}+R_5$

Use of this processing technique can eliminate the shimmering artifact as a result of realignment of the image pixels from image line to image line. Although the image pixels are not sampled perfectly uniformly in theory, the sampling error is negligibly small when the image lines are processed with a [1 3 3 1] or higher order filter.

Figure 7:
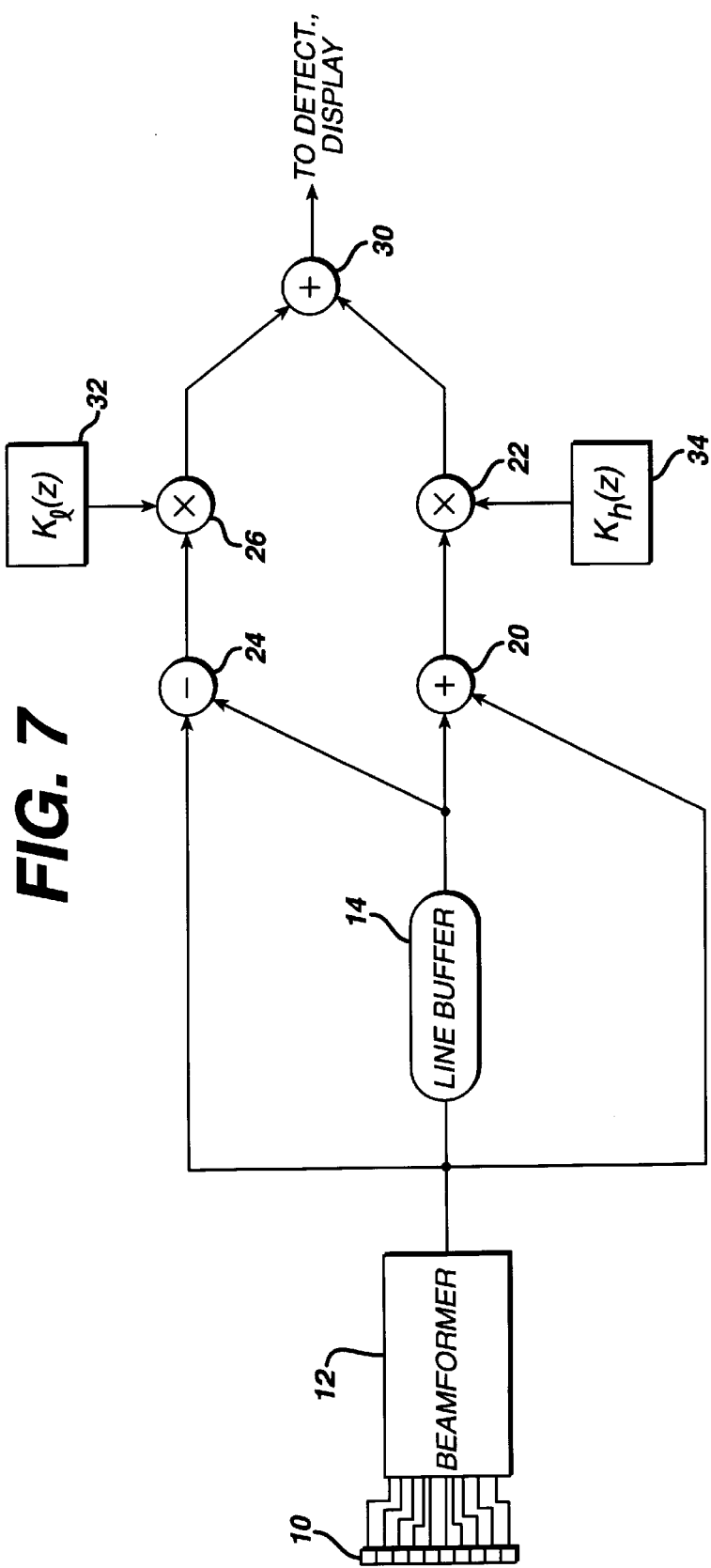
FIG. 7 illustrates in block diagram form the receiver of an ultrasonic diagnostic imaging system for producing both separated fundamental and harmonic signals which are blended into a common image.

FIG. 7 illustrates a processing system which simultaneously separates both linear and harmonic echo signal components, then blends them together in a single image as a function of depth. Such a blended image can take advantage of the low nearfield clutter performance which is possible with harmonic components, and the better depth penetration of linear components. In FIG. 7 the summer 20 additively combines sequential scanlines received from oppositely phased transmit signals to produce separated harmonic signal components as in the case of the embodiment of FIG. 5. A subtractor 24 takes the difference of sequential scanlines received from oppositely phased transmit signals to produce separated linear (fundamental) signals. The signals from the summer 20 and subtractor 24 can if desired be separately processed and displayed as separate or overlaid harmonic and fundamental images. In this embodiment the respective harmonic and fundamental signals are multiplied by weighting functions by multipliers 22 and 26. The harmonic signal components are weighted by a depth-variable weighting factor $k_h(z)$. The linear signal components are also weighted by a depth-variable weighting factor $k_l(z)$. In a preferred embodiment the weighting factors vary in an inverse relationship, with harmonic components more heavily weighted in the near field and linear components more heavily weighted in the far field. The weighted signal components are combined by a summer 30, then forwarded for detection, image processing, and display.

It will be appreciated that other factors can be used to control the variability of the weighting factors such as other spatial dimensions or time. Variable blending can take advantage of the different characteristics of linear and harmonic signals in different imaging applications.

Figure 4:
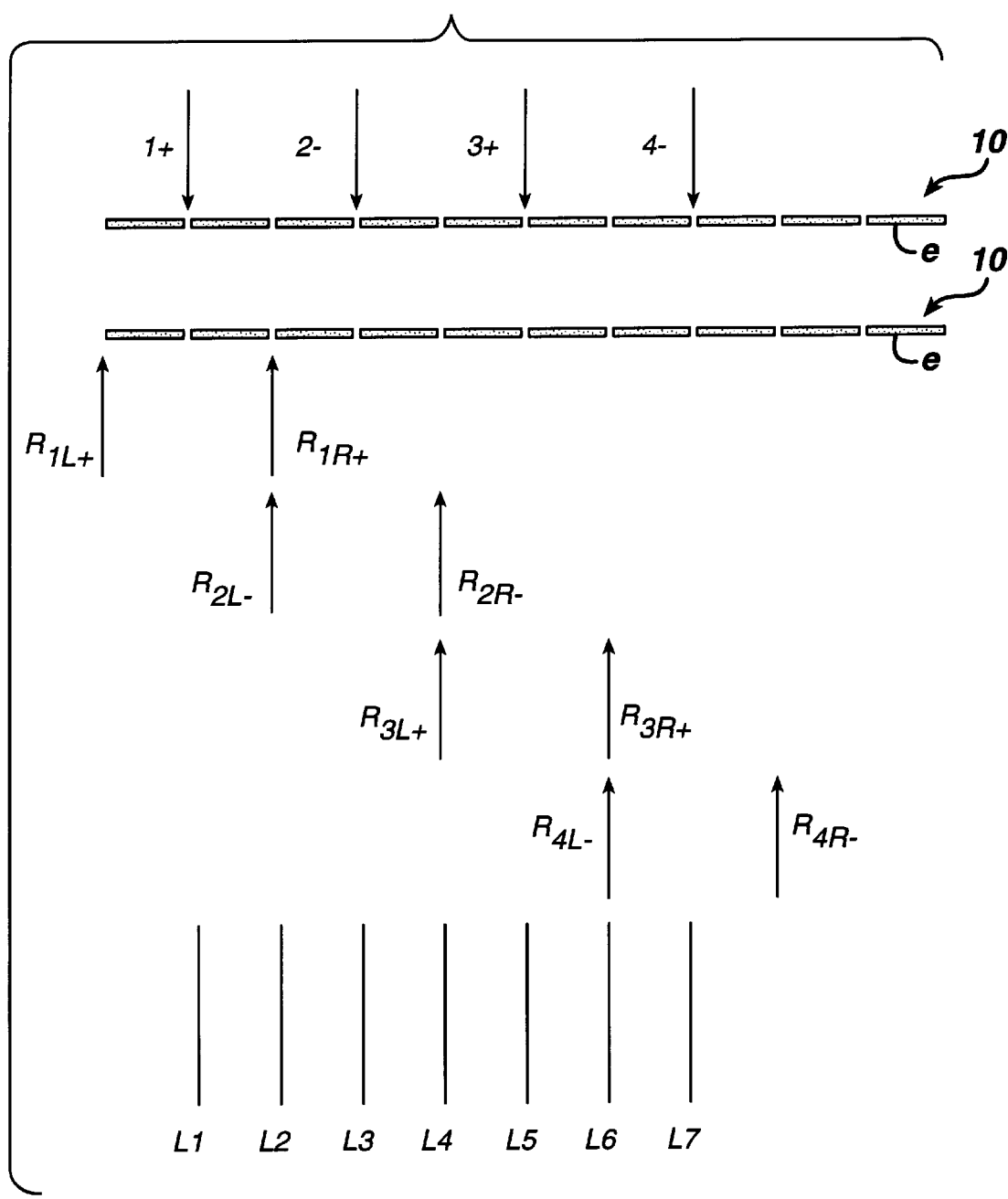
FIG. 4 illustrates a pulse inversion scanning technique of the present invention using multiline scanline reception.

An embodiment of the present invention producing an even greater frame rate of display is shown in FIG. 4. In this embodiment only a single transmit scanline is produced at a two element spacing. The polarity or phasing of the transmit pulses alternates from one transmit scanline to the next. The acoustic field of each transmitted scanline is broad enough to encompass two receive scanlines which are simultaneously received, as shown in U.S. Pat. No. 4,644,795. Thus, "multiline" reception is employed for multiple scanlines following each transmit wave. In the illustrated embodiment transmit scanline 1+ results in the reception of a receive scanline to the right and left of the center of the transmit aperture, $R_{1L+}$ and $R_{1R+}$. Similarly, transmit scanline 2− results in the reception of receive scanlines $R_{2L-}$ and $R_{2R-}$, and transmit scanline 3+ results in the reception of receive scanlines $R_{3L+}$ and $R_{3R+}$, and so on. In this embodiment the received scanlines are spaced one element to the left and right of the transmit scanline so that successive received scanlines are in alignment, however, this is not required; the technique is applicable even when the received scanlines do not overlap, although care must be taken to avoid artifacts from spatial aliasing when greater scanline spacing is employed.

Successively received scanlines are then combined to produce separated harmonic (or linear) signals along the image lines depicted at the bottom of FIG. 4. Image line L1 is formed by combining received scanlines $R_{1L+}$ and $R_{2L-}$, which are derived from oppositely phased transmit signals. Image line L2 is formed by combining received scanlines $R_{1R+}$ and $R_{2L-}$, which are likewise derived from oppositely phased transmit signals. Image line L3 can be formed by combining $R_{1R+}$ and $R_{2R-}$, or by combining $R_{2L-}$ and $R_{3L+}$. Like the embodiment of FIG. 3, each image line is aligned with one of the transmit or receive apertures, and unaligned with respect to the other, which is split on either side of the image line. These image lines are subject to the same artifacts as the FIG. 3 technique, and thus benefit from higher order filtering. Using the [1 3 3 1] filter, image line L2 is formed by combining received scanlines $R_{1L+}+3R_{1R+}+3R_{2L-}+R_{2R-}$ which are derived from consecutive, oppositely phased transmit signals. Image line L3 is formed by combining received scanlines $R_{1R+}+3R_{2L-}+3R_{2R-}+R_{3L+}$, which are likewise derived from consecutive, oppositely phased transmit signals. Image line L4 can be formed by combining $R_{2L-}+3R_{2R-}+3R_{3L+}+R_{3R+}$. Like the embodiment of FIG. 3, each image line is aligned with one of the transmit or receive apertures, and unaligned with respect to the other, which is split on either side of the image line. Thus, this filtering technique has the same beneficial artifact performance as in the embodiment of FIG. 3.

Figure 8:
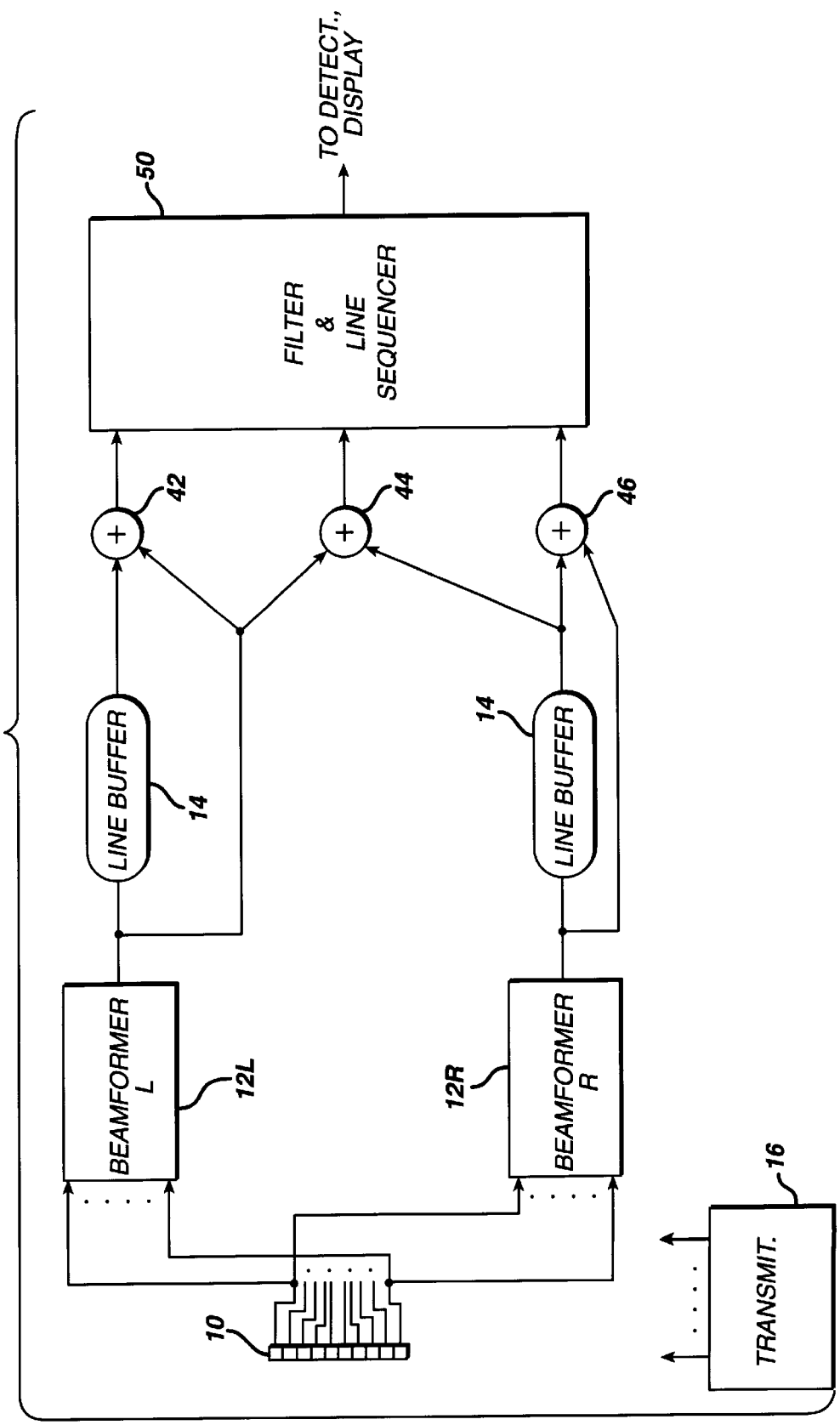
FIG. 8 illustrates in block diagram form the receiver of an ultrasonic diagnostic imaging system using multiline reception for producing pulse inversion separated harmonic signals in accordance with the principles of the present invention.

An ultrasound receive signal processor for performing the scanning technique of FIG. 4 is shown in FIG. 8. In this system the elements of the transducer array 10 are coupled to individual channels of a transmitter 16, which provide individually timed transmit signals to each element to steer and focus the transmit scanline beam as desired. The transducer elements are also coupled in parallel to the inputs of two receive beamformers, beamformer 12L and beamformer 12R, preferably by multiplexing which enables the inputs to the beamformers to be changed so that they may be operated as two multiline beamformers or as one single-line beamformer. The received scanlines produced by the two beamformers are coupled to the inputs of line buffers 14 and to the inputs of summers 42, 44, and 46. The summers combine sequential scanlines from opposite polarity transmit pulses and produce image lines of separated harmonic echo components. Separated linear signal components can be obtained by the use of sign change circuits at the output of each beamformer (not shown) to change the sign of signals received from alternate transmit pulses. A filter and line sequencer 50 receives image line data from the three summers, buffers the data as required, and transmits image line data to the detection, processing and display circuitry of the ultrasound system in a desired image line sequence. Alternatively, the filter and line sequencer can comprise a multiple entry frame store which stores multiple selected image lines for subsequent processing and display.

In operation, beamformer 12L will sequentially produce scanlines $R_{1L+}$, $R_{2L-}$, $R_{3L+}$, $R_{4L-}$, and so on in response to the transmit scanline sequence of FIG. 4. The beamformer 12R will concurrently produce scanlines $R_{1R+}$, $R_{2R-}$, $R_{3R+}$, $R_{4R-}$, and so on. These sequences result in the production of the following combinations at the outputs of the summers:

$(R_{1L+}+R_{2L-})$ $(R_{2L-}+R_{1R+})$ $(R_{1R+}+R_{2R-})$ $(R_{2R-}+R_{3L+})$ $(R_{3L+}+R_{4L-})$ $(R_{4L-}+R_{3R+})$ $(R_{3R+}+R_{4R-})$ ...

where this sequence of image lines is produced by summer 42, summer 44, summer 46, summer 44, summer 42, summer 44, summer 46, and so on. Sequencing the summer outputs in this order will produce the image line sequence L1, L2, L3, L4, L5, and so on as shown at the bottom of FIG. 4.

Since the scanning technique of FIG. 4 will benefit by the same filtering techniques as the previous embodiment, in a preferred embodiment of FIG. 8, the filter and line sequencer 50 processes the scanline data with a [1 3 3 1] filter in the same manner as the previous embodiment. This will lead to the production of harmonic signal components of the form:

L2: $(R_{1L+}+3R_{1R+}+3R_{2L-}+R_{2R-})$
L3: $(R_{1R+}+3R_{2L-}+3R_{2R-}+R_{3L+})$
L4: $(R_{2L-}+3R_{2R-}+3R_{3L+}+R_{3R+})$
L5: $(R_{2R-}+3R_{3L+}+3R_{3R+}+R_{4L-})$
L6: $(R_{3L+}+3R_{3R+}+3R_{4L-}+R_{4R-})$

By inverting the sign of the received data acquired in response to the transmit pulses of inverted (negative) sign or polarity, the [1 3 3 1] filter will produce linear signal components of the form:

L2: $(R_{1L+}+3R_{1R+}-3R_{2L-}-R_{2R-})$
L3: $(R_{1R+}-3R_{2L-}-3R_{2R-}+R_{3L+})$
L4: $(-R_{2L-}-3R_{2R-}+3R_{3L+}+R_{3R+})$
L5: $(-R_{2R-}+3R_{3L+}+3R_{3R+}-R_{4L-})$
L6: $(R_{3L+}+3R_{3R+}-3R_{4L-}-R_{4R-})$

The principles of the pulse inversion scanning technique of FIG. 4 can be applied to the interpolation of multiline received signals to cure a defect of prior art arrangements. The simplest conventional multiline sequence is to receive two scanlines for every transmit pulse, one scanline on either side of the center of the transmit beam. One prior art interpolation technique forms one image line by averaging the two received scanlines, and another image line by averaging adjacent scanlines from two consecutive transmit pulses, that is, the scanline to the left of one transmit beam is averaged with the scanline to the right of the neighboring transmit beam. Received scanlines across the image field are averaged in this manner to develop an image of interpolated scanlines. This interpolation technique is susceptible to an alternating motion artifact similar to that described above, because the first pair of scanlines (and every odd-numbered pair) which are averaged are concurrently received and the second pair of scanlines (and every even-numbered pair) which are averaged are sequentially received. If there is motion in the image field, the concurrently received scanlines will be equally affected because they are produced by a single transmit pulse. The sequentially received scanlines will be differently affected by motion because they are developed by temporally different transmit pulses and each scanline will reflect the position of moving materials as of the moment they are produced. Thus, odd-numbered lines will not have a motion artifact and even-numbered lines will, creating a scintillation-type artifact when there is motion in the image plane.

Figure 9:
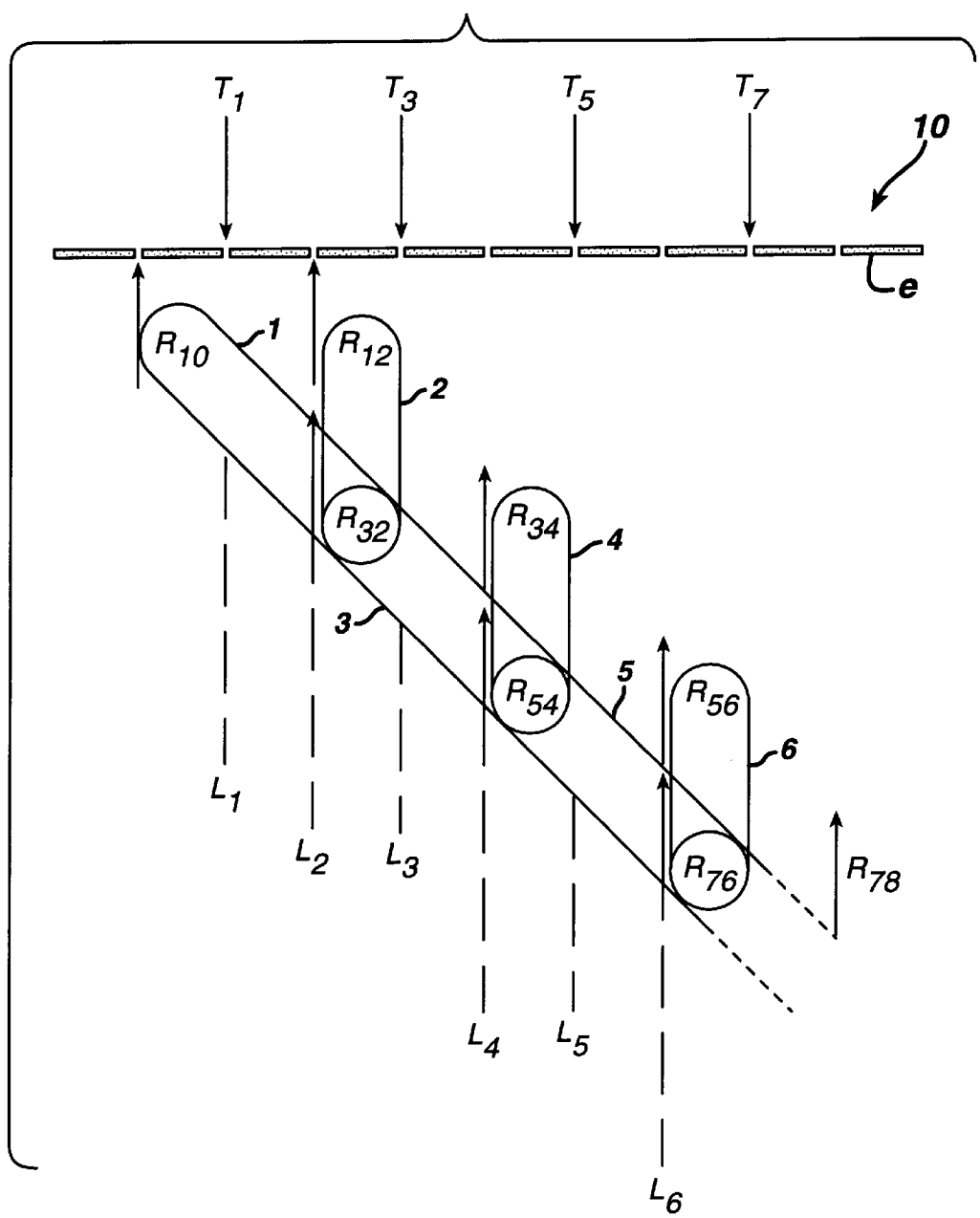
FIG. 9 illustrates application of the principles of the present invention in single pulse imaging to reduce motion artifacts.

In accordance with a further aspect of the present invention, this motion artifact of multiline interpolation is avoided as shown in FIG. 9. In this drawing a sequence of transmit pulses $T_1$, $T_3$, $T_5$, ... is transmitted across the image field. A pair of scanlines are received in response to each transmit pulse. For instance, scanlines $R_{10}$ and $R_{12}$ are received in response to transmit pulse $T_1$, where the first subscript refers to the number of the transmit pulse which produced the scanline, and the second subscript refers to the relative position of the received scanline across the image field. The second transmit pulse $T_3$ results in the reception of scanlines $R_{32}$ and $R_{34}$, and so on.

The prior art technique for forming interpolated image lines from these scanlines is to average $R_{10}$ and $R_{12}$ to form image line L1; $R_{12}$ and $R_{32}$ to form image line L2; and so on across the image field. But L1 is formed from temporally identical received scanlines and L2 is formed from temporally different received scanlines, giving rise to the motion artifact. The technique of the present invention overcomes this problem by consistently forming image lines from temporally different received scanlines. That is, L1 is formed by interpolating scanlines $R_{10}$ and $R_{32}$, image line L2 is formed by interpolating scanlines $R_{12}$ and $R_{32}$, image line L3 is formed by interpolating scanlines $R_{32}$ and $R_{54}$, and so on as shown by the ovals 1, 2 and 3 encompassing these scanline designators in FIG. 9. This results in a uniform characteristic of the interpolated image lines across the image field, since each image line is formed from two temporally different scanlines. This method of interpolation is continued across the image field as the encompassing ovals 4, 5, and 6 in FIG. 9 indicate.

The present inventor has noted that, while the above two-line interpolation technique reduces the motion scintillation artifact, an error is introduced by the variation in the locations of the transmit and receive apertures from line to line across the image field. Hence, the present inventor prefers the use of a three-line lateral filter of the form $(R_x+2R_y+R_z)$ for use as the line interpolator for FIG. 9. This set of filter coefficients advantageously weights two scanlines acquired on one side of a transmit beam with a double-weighting of a scanline acquired on the other side. This filter will form image line L1 by interpolating scanlines $R_{10}$, $2R_{12}$ and $R_{32}$; image line L2 is formed by interpolating scanlines $R_{12}$, $2R_{32}$, and $R_{34}$; image line L3 is formed by interpolating scanlines $R_{32}$, $2R_{34}$ and $R_{54}$, and so on. This filter form is also effective for performing high frame rate pulse inversion harmonic separation. Referring to FIG. 4, for instance, it may be seen that a lateral filter of this form will sequentially produce $(R_{1L+}+2R_{2L-}+R_{1R+})$ $(R_{2L-}+2R_{1R+}+R_{2R-})$ $(R_{1R+}+2R_{2R-}+R_{3L+})$ This sequence is seen to combine two weights of scanlines received from positive (or negative) polarity transmit pulses with two weights of scanlines received from negative (or positive) polarity transmit pulses, thereby providing complete harmonic separation.

The image line interpolation technique of FIG. 9 can be carried out by the multiline receiver and interpolation arrangement of FIG. 10. In this system the elements e of the array transducer 10 are individually driven by a transmitter 136 to steer a focused transmit beam from the desired point along the transducer array in the desired direction in the image field. Conductors or, preferably, multiplexers couple echo signals received by the elements e to a multiline beamformer 132,134, as indicated by the arrow 130. The multiline beamformer 132,134 may be two separate beamformers, or separately controllable and separately summing partitions of a single beamformer. Each multiline beamformer partition produces a received scanline, one to the left and one to the right of the transmit beam transmitted under control of transmitter 136. Each pair of concurrently received scanlines is stored temporarily in a line memory 138 which acts as a buffer, and forwarded at the appropriate time with subsequently received scanlines to line interpolator 140. The line interpolator forms an image line by interpolating pairs of scanlines as shown in FIG. 9, or preferably implements a three-line [1 2 1] lateral filter of the form $(R_x+2R_y+R_z)$. The interpolated image lines are coupled to detection and signal processing circuitry 142 and a scan converter 146 for processing and display of an image on a display 150. It is seen that the apparatus of FIG. 10 when operated in accordance with the technique of FIG. 9 can form high frame rate interpolated multiline images of virtually every sort of echo signal. This apparatus and technique will find use in B mode, Doppler and harmonic imaging.

What is claimed is:

1. A method for producing high frame rate or line density ultrasonic harmonic images comprising the steps of:

transmitting a first ultrasonic beam of a given phase or polarity and at a fundamental frequency along a first beam direction;

transmitting a second ultrasonic beam of a different phase or polarity and at said fundamental frequency along a second beam direction adjacent to said first beam direction;

receiving echoes in response to each transmitted beam; and combining said received echoes from said transmitted beams on a spatial basis to produce separated harmonic echoes along a beam direction intermediate said first and second beam directions.

2. The method of claim 1, wherein said step of receiving comprises receiving echoes containing fundamental frequency components and harmonic frequency components.

3. The method of claim 2, wherein said step of combining comprises additively combining said received echoes on a spatial basis to cancel fundamental frequency components and reinforce harmonic frequency components.

4. The method of claim 3, wherein said spatial basis comprises a common receive depth basis.

5. The method of claim 1, further comprising the steps of:

transmitting a third ultrasonic beam of said different phase or polarity and at said fundamental frequency along said first beam direction;

receiving echoes in response to said third transmitted beam; and combining said received echoes from said first and third transmitted beams on a spatial basis to produce separated harmonic echoes along said first beam direction.

6. The method of claim 5, further comprising the steps of:

transmitting a fourth ultrasonic beam of said given phase or polarity and at said fundamental frequency along said second beam direction;

receiving echoes in response to said fourth transmitted beam; and combining said received echoes from said second and fourth transmitted beams on a spatial basis to produce separated harmonic echoes along said second beam direction.

7. An ultrasonic diagnostic imaging system which produces harmonic images comprising:

an array transducer;

a beamformer, coupled to said array transducer, which controls said array transducer to transmit first and second ultrasonic beams at a fundamental frequency and at different phases or polarities along first and second beam directions, and which forms echoes in response to each transmitted beam; and a combiner, coupled to said beamformer, which combines said echoes on a spatial basis to produce separated harmonic echoes along a beam direction intermediate said first and second beam directions; and an image processor, coupled to said combiner, for producing ultrasonic image signals in response to said combined echoes.

8. The ultrasonic diagnostic imaging system of claim 7, wherein said beamformer further comprises means for forming echoes containing fundamental frequency components and harmonic frequency components in response to each transmitted beam.

9. The ultrasonic diagnostic imaging system of claim 7, wherein said combiner further comprises means for combining echoes formed in response to said first and second beams on a common receive depth basis.

10. The ultrasonic diagnostic imaging system of claim 7, further comprising an echo storage unit, coupled to said beamformer and said combiner, which stores echoes formed in response to a transmitted beam.

11. The ultrasonic diagnostic imaging system of claim 7, further comprising means for combining said echoes on a spatial basis to produce separated fundamental frequency echoes along a beam direction intermediate said first and second beam directions.

12. The ultrasonic diagnostic imaging system of claim 11, wherein said combiner comprises means for additively combining said echoes, and wherein said combining means comprises means for subtractively combining said echoes.

13. The ultrasonic diagnostic imaging system of claim 11, wherein said combiner comprises a summer, and wherein said combining means comprises a difference circuit.

14. The ultrasonic diagnostic imaging system of claim 11, wherein said combining means further comprises a sign change circuit coupled to said beamformer and said combiner, wherein said combiner alternately produces separated fundamental or harmonic frequency echoes as determined by the operation of said sign change circuit.

15. A method for producing high frame rate or line density ultrasonic harmonic images comprising the steps of:

transmitting a sequence of opposing phase or polarity waveforms at a fundamental frequency;

receiving scanline echo data in response to said transmitted waveforms; and convolving said scanline echo data with a lateral filter of at least three received scanlines in width to produce separated harmonic echoes.

16. The method of claim 15, wherein said lateral filter is of the form [1 2 1].

17. The method of claim 16, wherein said lateral filter produces harmonic components of the form $(R_{1+}+2R_{2-}+R_{3+})$ and $(R_{2-}+2R_{3+}+R_{4-})$.

18. The method of claim 15, wherein said lateral filter is of the form [1 3 3 1].

19. The method of claim 18, wherein said lateral filter produces harmonic components of the form $(R_{1+}+3R_{2-}+3R_{3+}+R_{4-})$ and $(R_{2-}+3R_{3+}+3R_{4-}+R_5)$.

20. A method for producing high frame rate or line density ultrasonic harmonic images comprising the steps of:

transmitting a sequence of fundamental frequency, laterally spaced beams of opposing phase or polarity;

receiving at least two laterally spaced scanlines in response to respective ones of said transmit beams; and combining two or more received scanlines from opposing phase or polarity beams to produce lines of separated harmonic echo information at locations intermediate said combined scanlines.

21. The method of claim 20, wherein the step of transmitting transmits a sequence of laterally separated beams of the form 1+, 2−, 3+, 4−.

22. The method of claim 21, wherein the step of receiving receives pairs of scanlines of the form $(R_{1L+},R_{1R+})$, $(R_{2L-}, R_{2R-})$ $(R_{3L+},R_{3R+})$, $(R_{4L-},R_{4R-})$.

23. The method of claim 22, wherein the step of combining produces lines of separated harmonic echo information of the form $(R_{1L+}+R_{2L-})$, $(R_{1R+}+R_{2L-})$, $(R_{3L+}+R_{2L-})$, $(R_{2R-}+R_{3L+})$.

24. The method of claim 22, wherein the step of combining comprises the step of laterally filtering two or more received scanlines of opposing phase or polarity beams.

25. The method of claim 24, wherein the step of laterally filtering comprises using a filter function of the form [1 2 1] to produce lines of separated harmonic echo information of the form $(R_{1L+}+2R_{2L-}+R_{1R+})$, $(R_{2L-}+2R_{1R+}+R_{2R-})$, $(R_{2L-}+2R_{3L+}+R_{2R-})$, $(R_{3L+}+2R_{2R-}+R_{3R+})$.

26. The method of claim 24, wherein the step of laterally filtering comprises using a filter function of the form [1 3 3 1] to produce lines of separated harmonic echo information of the form $(R_{1L+}+3R_{1R+}+3R_{2L-}+R_{2R-})$, $(R_{1R+}+3R_{2L-}+3R_{2R-}+R_{3L+})$, $(R_{2L-}+3R_{2R-}+3R_{3L+}+R_{3R+})$, $(R_{2R-}+3R_{3L+}+3R_{3R+}+R_{4L-})$.

27. The method of claim 1, further comprising the steps of:

transmitting a third ultrasonic beam of said given phase or polarity and at a fundamental frequency along a third beam direction adjacent to said second beam direction;

receiving echoes in response to said third transmitted beam; and combining said received echoes from said second and third transmitted beams on a spatial basis to produce separated harmonic echoes along a beam direction intermediate said second and third beam directions.

* * * * *